United States Patent [19]

Rizzo et al.

[11] Patent Number: 4,892,956

[45] Date of Patent: Jan. 9, 1990

[54] 5-CYANO-4,5-DIHYDRO-3,4-DICARBOXYPYRAZOLE DERIVATIVES

[75] Inventors: John R. Rizzo; Eddie V. P. Tao, both of Indianapolis, Ind.

[73] Assignee: Eli Lilly and Company, Indianapolis, Ind.

[21] Appl. No.: 267,905

[22] Filed: Nov. 7, 1988

[51] Int. Cl.[4] .......................................... C07D 231/06
[52] U.S. Cl. .................................... 548/356; 548/378
[58] Field of Search ........................................ 548/356

[56] References Cited

U.S. PATENT DOCUMENTS 4,589,905  5/1986  Beck ......................................... 71/66

OTHER PUBLICATIONS

Pyrazoles, Pyrazolines, Pyrazolidines, Indazoles and Condensed Rings, edited by Richard Wiley (1967), p. 198.
Kalvoda, *Collection of Czechoslovakian Chemistry*, 40, 1431 (1970).
Lantos et al., *J. Org. Chem.*, 43(25), 4841 (1978).
Jones et al., *J. Org. Chem.*, 20, 1342 (1955).
*Introduction to Organic Chemistry*, Streitweiser et al., ed., 1091–1094 (1976).

*Primary Examiner*—Robert W. Ramsuer
*Attorney, Agent, or Firm*—Douglas J. Taylor; Leroy Whitaker

[57] ABSTRACT

The present invention provides 5-cyano-4,5-dihydro-3,4-dicarboxypyrazoles and a process for preparing such compounds which comprises reacting a dialkyl fumarate with diazoacetonitrile.

3 Claims, No Drawings

5-CYANO-4,5-DIHYDRO-3,4-DICARBOX-YPYRAZOLE DERIVATIVES

BACKGROUND OF THE INVENTION

U.S. Pat. No. 4,589,905 discloses herbicides and algicides which are 1-alkyl-5-cyano-1H-pyrazole-4-carboxamides. The compounds are prepared by a multi-step process which includes reacting an alkylhydrazine with an alkyl α-acetyl-α-(dimethylaminomethylene)acetate to produce a 5-methyl-1-alkyl-1H-pyrazole-4-carboxylic acid ester, followed by conversion of the 4-carboxyl and 5-methyl groups to carboxamide and cyano groups, respectively.

This invention concerns the synthesis of 5-cyano-4,5-dihydro-3,4-dicarboxypyrazoles which are intermediates for the herbicides and algicides of U.S. Pat. No. 4,589,905. The process of the invention produces the pyrazole intermediates in high yield and purity, while employing inexpensive starting materials. Thus, an object of the present invention is to provide an economical and efficient process for preparing certain substituted pyrazoles. A second object of the present invention is to provide new compounds; namely, 5-cyano-4,5-dihydro-3H-pyrazole-3,4-dicarboxylic acid dialkyl esters, which are useful intermediates.

SUMMARY OF THE INVENTION

This invention provides a process for preparing 5-cyano-4,5-dihydro-3H-pyrazole-3,4-dicarboxylic acid dialkyl esters of the formula

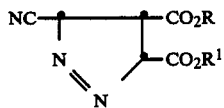

wherein R and $R^1$ are independently $C_1$–$C_{10}$ alkyl, comprising reacting a dialkyl fumarate of the formula

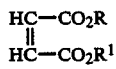

with diazoacetonitrile.

In a preferred embodiment, the process employs dialkyl fumarates wherein R and $R^1$ are independently $C_1$–$C_6$ alkyl. A more preferred embodiment employs dialkyl fumarates wherein R and $R^1$ are the same and are $C_1$–$C_6$ alkyl. The most preferred process of the present invention comprises reacting diethyl fumarate with diazoacetonitrile to produce 5-cyano-4,5-dihydro-3H-pyrazole-3,4-dicarboxylic acid diethyl ester.

This invention also provides the 5-cyano-4,5-dihydro-3H-pyrazole-3,4-dicarboxylic acid dialkyl esters of the above formula as new chemical compounds. Preferred compounds of the invention are those wherein R and $R^1$ are the same and are $C_1$–$C_6$ alkyl. The most preferred compound of the invention is 5-cyano-4,5-dihydro-3H-pyrazole-3,4-dicarboxylic acid diethyl ester.

DETAILED DESCRIPTION OF THE INVENTION

The term "$C_1$–$C_6$ alkyl" as used herein refers to straight and branched aliphatic groups of 1 to 6 carbon atoms such as methyl, ethyl, n-propyl, isopropyl, n-butyl, sec-butyl, isobutyl, n-butyl, n-pentyl, tert-pentyl, 3-pentyl, n-hexyl, 2,3-dimethylbutyl, and the like.

The term "$C_1$–$C_{10}$ alkyl" includes the foregoing groups as well as $C_7$–$C_{10}$ groups such as n-heptyl, n-octyl, 3-ethylhexyl, 2,4-dimethylhexyl, n-nonyl, 2,3,4-trimethylhexyl, n-decyl, and the like.

The 5-cyano-4,5-dihydro-3H-pyrazole-3,4-dicarboxylic acid dialkyl esters of the invention are prepared by reacting a dialkyl fumarate of the formula

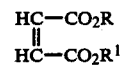

wherein R and $R^1$ are independently $C_1$–$C_{10}$ alkyl, with diazoacetonitrile. The dialkyl fumarate starting materials are either commercially available, described in the literature, or can be prepared by methods known in the art. Diazoacetonitrile may be prepared by reacting aminoacetonitrile with sodium nitrite according to methods well known in the art.

The dialkyl fumarate starting materials employed in the present invention can be symmetrical ($R^1$=R) or unsymmetrical ($R^1 \neq R$). Examples of typical fumarates which can be used include dimethyl fumarate, diethyl fumarate, dibutyl fumarate, dihexyl fumarate, methyl ethyl fumarate, ethyl propyl fumarate, methyl pentyl fumarate, pentyl octyl fumarate, and the like.

If an unsymmetrical fumarate is employed, the reaction product will be a mixture of two isomeric compounds. For example, if ethyl butyl fumarate is reacted with diazoacetonitrile according to this invention, the products produced will be

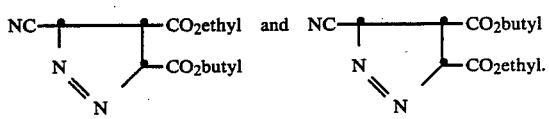

The isomers can be separated, if desired, by standard isolation techniques such as distillation, crystallization, column chromatography and the like. Alternatively, the isomeric mixture may be employed directly to synthesize the herbicides or algicides described in U.S. Pat. No. 4,589,905, with the isomers being separated at a later step in the synthesis.

Since the unsymmetrical fumarates produce a mixture of reaction products, symmetrical fumarates are preferred starting materials in the process of the present invention. Such symmetrical starting materials can be used to prepare 5-cyano-4,5-dihydro-3H-pyrazole-3,4-dicarboxylic acid dialkyl esters in high yield and purity, while also eliminating the need to employ expensive purification steps.

The process of the present invention comprises reacting a dialkyl fumarate with diazoacetonitrile in an inert solvent. Inert solvents are those in which the reactants are substantially soluble and which do not themselves undergo chemical reaction during the process. Examples of typical inert solvents which can be used in the process include halogenated alkanes such as methylene chloride, carbon tetrachloride, bromoform, 1,2-bromoethane, isopropyl chloride and the like; ethers such as diethyl ether, methyl ethyl ether, tetrahydrofuran and the like; ketones such as acetone, methyl ethyl ketone and the like; aromatic solvents such as toluene, benzene, chlorobenzene and the like; alcohols such as methanol, ethanol, isopropanol and the like: and esters such as ethyl acetate and the like. Preferred solvents are the esters, alcohols and aromatic solvents, with ethyl acetate being the most preferred solvent.

The concentrations of dialkyl fumarate and diazoacetonitrile in the inert solvent are not critical. In general, it is desirable to use as concentrated a solution as possible to minimize product loss during isolation. However, enough solvent should be used to ensure that the reactants remain substantially in solution during the reaction.

The relative amounts of diazoacetonitrile and dialkyl fumarate employed also are not critical. In general, at least an equimolar amount or slight excess of diazoacetonitrile relative to the dialkyl fumarate is used since the dialkyl fumarate reactant is more expensive. However, if an excess of dialkyl fumarate is employed, the additional cost associated with such reaction conditions can be reduced by recovering the unreacted fumarate reactant by extraction using an alkane solvent, such as hexane, and then re-using the recovered material in subsequent reactions. Ideally about 2.5 molar equivalents of diazoacetonitrile are employed relative to the dialkyl fumarate.

The reaction is generally conducted at a temperature of about 0° C. to about 50° C., with the most desired temperature being about room temperature (24° C.). The process is generally substantially complete after about 2 hours to about 72 hours when conducted at a temperature in the range of about 0° C. to about 50° C. The progress of the reaction can be followed, if desired, by standard techniques such as high performance liquid chromatography (HPLC).

The resulting 5-cyano-4,5-dihydro-3H-pyrazole-3,4-dicarboxylic acid dialkyl esters can be isolated by standard methods, if desired, but need not be. Regardless of whether isolated prior to further reaction, or reacted in-situ, the 5-cyano-4,5-dihydro-pyrazole-3,4-dicarboxylic acid dialkyl esters are readily converted to 1-alkyl-5-cyano-1H-pyrazole-4-carboxamide herbicides or algicides according to the synthesis of Reaction Scheme I below.

REACTION SCHEME I

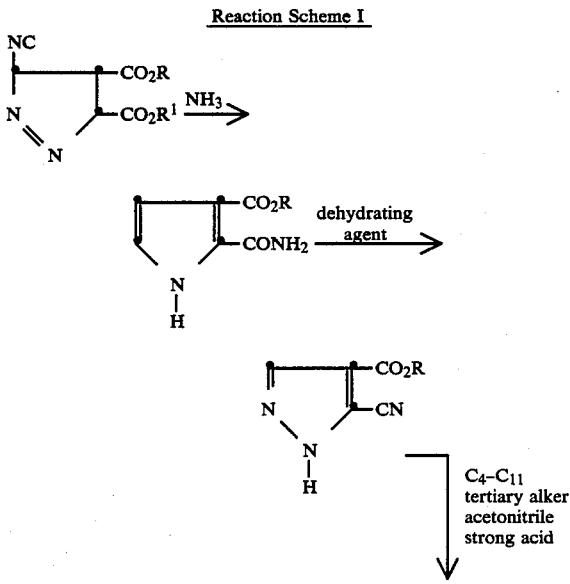

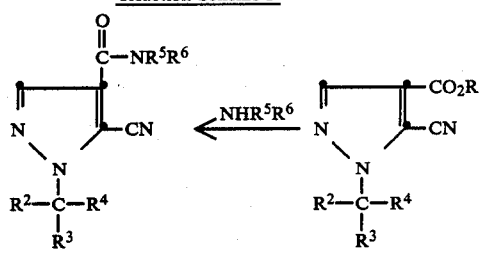

wherein R and $R^1$ are as defined previously; $R^2$ is $C_1$–$C_4$ alkyl; $R^3$ and $R^4$ independently are $C_1$–$C_3$ alkyl; and $R^5$ and $R^6$ independently are hydrogen, $C_1$–$C_4$ alkyl, $C_3$–$C_4$ alkenyl, $C_3$–$C_4$ alkynyl, $C_3$–$C_4$ cycloalkyl or $C_1$–$C_3$ alkoxy.

In Reaction Scheme I, the 5-cyano-4,5-dihydro-3H-pyrazole-3,4-dicarboxylic acid dialkyl esters of the invention are converted to 3(5)-carbamoyl-1H-pyrazole-4-carboxylic acid esters by reaction with at least two equivalents of ammonia. Alternatively, a base other than ammonia, for example triethylamine, pyridine, potassium carbonate, sodium hydroxide and the like, may be used. Bases other than ammonia simply effect removal of the cyano group to provide a 3,4-pyrazole dicarboxylic acid dialkyl ester, which, upon further reaction with ammonia, affords the corresponding 3-carboxamide derivative.

The carboxamide group at the 3(5)-position is then converted to a cyano group by reaction with a dehydrating agent such as phosphorus oxychloride. The 1-position of the pyrazole ring is alkylated by reacting the 3(5)-cyano-1H-pyrazole-4-carboxylic acid ester with an alkene and a strong acid in acetonitrile. Finally, the product herbicides or algicides may be prepared by reacting the compound which has a carboxylic acid ester moiety at the 4-position with an appropriately substituted amine to produce a carboxamide.

The following Examples illustrate specific aspects of the present invention. The Examples are not intended to limit the scope of the invention in any respect and should not be so construed.

EXAMPLE 1

5-Cyano-4,5-dihydro-3H-pyrazole-3,4-dicarboxylic acid diethyl ester

To a 500 ml, 3-neck, round bottom flask containing a cold (0° C.) slurry of 46.26 g (0.5 mol) of aminoacetonitrile hydrochloride and 32.74 ml (0.2 mol) of diethyl fumarate in 200 ml of ethyl acetate, were added dropwise, over one hour, an aqueous solution of sodium nitrite (34.5 g of sodium nitrite dissolved in 90 ml of water). The temperature of the reaction mixture was maintained between 0° C. and 5° C. during nitrite addition and then warmed to room temperature (24° C.), where the mixture was stirred for about 3 hours. The organic layer was separated from the aqueous layer and then stirred at room temperature overnight to provide a solution of title compound dissolved in ethyl acetate.

5-Cyano-4,5-dihydro-3H-pyrazole-3,4-dicarboxylic acid diethyl ester was converted to 3(5)-carbamoyl-1H-pyrazole-4-carboxylic acid ethyl ester in situ by adding 104 ml of a concentrated ammonium hydroxide solution (30%, by weight, ammonia in water) to the ethyl acetate solution prepared above. The resulting slurry was stirred for two days and then filtered. The recovered solid was washed with 5 ml of methanol and dried in a vacuum oven at 40° C. to provide 25.54 g (77.9% yield) of 3(5)-carbamoyl-1H-pyrazole-4-carboxylic acid ethyl ester.

m.p. >300° C. Analysis calculated for $C_7H_9N_3O_3$: Theory: C, 45.90; H, 4.95; N, 22.90; Found: C, 45.66; H, 5.06; N, 23.21.

EXAMPLE 2

1-t-Butyl-5-cyano-N-methyl-1H-pyrazole-4-carboxamide

A. Preparation of 3(5)-carbamoyl-1H-pyrazole-4-carboxylic acid ethyl ester.

To a one liter round bottom flask containing a cold (0° C.) slurry of 67.6 g (0.6756 mol) of aminoacetonitrile hydrochloride and 44.2 ml (0.2702 mol) of diethyl fumarate in 300 ml of ethyl acetate, were added dropwise, over one hour, an aqueous solution of 46.6 g (0.6756 mol) of sodium nitrite dissolved in 90 ml of water. The temperature of the reaction mixture was maintained at about 0° C. during the nitrite addition, then warmed to room temperature (24° C.) where the mixture was stirred for about 3 hours. The organic layer was separated from the aqueous layer and then stirred at room temperature overnight to provide a solution of 5-cyano-4,5-dihydro-3H-pyrazole-3,4-dicarboxylic acid diethyl ester dissolved in ethyl acetate.

The next morning 280 ml of a concentrated ammonium hydroxide solution (30%, by weight, ammonia in water) were added to the ethyl acetate solution. The resulting slurry was stirred at 24° C. for twenty-four hours and filtered. The recovered solid was combined with 200 ml of methanol and the resulting slurry was filtered. The recovered solid was dried in a vacuum oven at 40° C. to provide 35.2 g (71.2% yield) of 3(5)-carbamoyl-1H-pyrazole-4-carboxylic acid ethyl ester.

B. Conversion to 1-t-butyl-5-cyano-N-methyl-1H-pyrazole-4-carboxamide

To a 500 ml round bottom flask were added 35.2 g (0.1923 mol) of the carbamoyl acid ester produced above, 8.77 g (0.0635 mol) of potassium carbonate, and 200 ml of acetonitrile. The mixture was heated to reflux (about 80° C.) and 13.44 ml (0.1443 mol) of phosphorus oxychloride were added. The reaction mixture was stirred at the reflux temperature for 4 hours, cooled to room temperature (24° C.), and then filtered to remove potassium chloride salts and any excess potassium carbonate.

The filtrate was placed into a pressure reactor along with 38.5 ml (0.3846 mol) of isobutylene and 12.07 g (0.0635 mol) of p-toluenesulfonic acid. The resulting solution was stirred at about 100° C. in the closed vessel for about 72 hours. The reaction was substantially complete by HPLC analysis, so the reaction solution was cooled to room temperature (24° C.) and the reactor vented to atmospheric pressure. The solution was concentrated to an oil by evaporation of the acetonitrile solvent under reduced pressure.

The oil was dissolved in 50 ml of methanol. Aqueous methylamine (89.6 ml of a 40%, by weight, solution of methylamine in water; 1.154 moles of methylamine) was added and the resulting solution stirred overnight at room temperature (24° C.). Solids (12.75 g) precipitated overnight and were recovered by filtration.

The filtrate was concentrated to an oil by removal of unreacted methylamine and methanol under reduced pressure. Water (100 ml) was added to the oil and the solution refrigerated overnight. Solids precipitated and were recovered by filtration. These solids were purified by dissolving them in 20 ml of dimethylformamide and then adding 50 ml of water. Purified solids (3.25 g) precipitated which were recovered by filtration.

All solids obtained from the oil described above were combined to provide 16.0 g (40.4% yield) of 1-t-butyl-5-cyano-N-methyl-1H-pyrazole-4-carboxamide. The product was shown to be 97.9% pure by HPLC and had a melting point of 162°–165° C.

Analysis calc. for $C_{10}H_{14}N_4O$: Theory: C, 58.2; H, 6.84; N, 27.17; Found: C, 58.27; H, 6.91; N, 26.95.

We claim:

1. A 5-cyano-4,5-dihydro-3H-pyrzole-3,4-dicarboxylic acid dialkyl ester of the formula

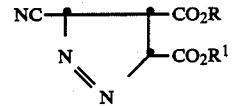

wherein R and $R^1$ are independently $C_1$–$C_{10}$ alkyl.

2. A compound of claim 1 wherein R and $R^1$ are the same and are $C_1$–$C_6$ alkyl.

3. The compound of claim 2 wherein R and $R^1$ are ethyl; namely, 5-cyano-4,5-dihydro-3H-pyrazole-3,4-dicarboxylic acid diethyl ester.

* * * * *